(12) United States Patent
Fautz

(10) Patent No.: US 11,598,833 B2
(45) Date of Patent: Mar. 7, 2023

(54) SATURATION-PREPARED RECORDING OF MR IMAGE DATA

(71) Applicant: Siemens Healthcare GmbH, Erlangen (DE)

(72) Inventor: Hans-Peter Fautz, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 82 days.

(21) Appl. No.: 17/308,140

(22) Filed: May 5, 2021

(65) Prior Publication Data
US 2021/0373101 A1 Dec. 2, 2021

(30) Foreign Application Priority Data

May 26, 2020 (DE) .................... 10 2020 206 515.2

(51) Int. Cl.
| | | |
|---|---|---|
| *G01R 33/483* | (2006.01) | |
| *G06T 11/00* | (2006.01) | |
| *A61B 5/055* | (2006.01) | |
| *A61B 5/026* | (2006.01) | |
| *G01R 33/56* | (2006.01) | |

(52) U.S. Cl.
CPC .......... *G01R 33/4835* (2013.01); *A61B 5/026* (2013.01); *A61B 5/055* (2013.01); *G01R 33/5608* (2013.01); *G06T 11/003* (2013.01); *G06T 2210/41* (2013.01)

(58) Field of Classification Search
None
See application file for complete search history.

(56) References Cited

U.S. PATENT DOCUMENTS

| 5,447,155 | A | | 9/1995 | Nessaiver et al. |
| 5,492,124 | A | * | 2/1996 | Purdy .................. G01R 33/563 |
| | | | | 600/419 |

(Continued)

FOREIGN PATENT DOCUMENTS

CN 1212145 A * 3/1999 ......... G01R 33/4833

OTHER PUBLICATIONS

Google Translation of German Office Action for German Application No. 10 2020 206 515.2, dated Apr. 21, 2021. (Year: 2021).*

(Continued)

*Primary Examiner* — Rodney E Fuller
(74) *Attorney, Agent, or Firm* — Lempia Summerfield Katz LLC

(57) ABSTRACT

A method is provided for the saturation-prepared recording of MR image data. The method includes establishment of at least two measurement slices in an examination volume of an examination object, wherein the examination volume has adjacent slices which each adjoin at least one of the at least two measurement slices; output of a saturation module including at least one saturation pulse for saturating a magnetization of the adjacent slices; output of an excitation pulse for exciting a magnetization of at least one of the at least two measurement slices; readout of an MR signal of the examination volume; reconstruction of the MR image data from the at least two measurement slices based on the MR signal; and provision of the MR image data. The disclosure further relates to a magnetic resonance system and a computer program product.

15 Claims, 7 Drawing Sheets

(56) References Cited

U.S. PATENT DOCUMENTS

| | | | | |
|---|---|---|---|---|
| 5,857,970 | A | * | 1/1999 | Purdy .............. G01R 33/56308 600/419 |
| 6,320,377 | B1 | | 11/2001 | Miyazaki et al. |
| 2014/0167752 | A1 | * | 6/2014 | Hanada ................ G01R 33/561 324/318 |

OTHER PUBLICATIONS

Felmlee, Joel P., and Richard L. Ehman "Spatial presaturation: a method for suppressing flow artifacts and improving depiction of vascular anatomy in MR imaging." Radiology 164.2 (1987): 559-564.
German Office Action for German Application No. 10 2020 206 515.2 dated Apr. 21, 2021.
Li, Linqing, Karla L. Miller, and Peter Jezzard. "DANTE-prepared pulse trains: a novel approach to motion-sensitized and motion-suppressed quantitative magnetic resonance imaging." Magnetic resonance in medicine 68.5 (2012): 1423-1438.
MRIquestions.com, "Saturation Pulses", http://mriquestions.com/saturation-pulses.html, Apr. 28, 2020. pp. 1-2.

* cited by examiner

SATURATION-PREPARED RECORDING OF MR IMAGE DATA

The present patent document claims the benefit of German Patent Application No. 10 2020 206 515.2, filed May 26, 2020, which is hereby incorporated by reference in its entirety.

TECHNICAL FIELD

The present disclosure relates to a method for saturation-prepared recording of MR image data, a magnetic resonance system, and a computer program product.

BACKGROUND

In a magnetic resonance (MR) examination, an examination object, (e.g., a human and/or animal patient and/or an examination phantom), is frequently exposed to a relatively strong main magnetic field, (e.g., 1.5, 3, or 7 tesla). This may be made possible by positioning the examination object within a recording area of a magnetic resonance system. The positioning of the examination object within the relatively strong main magnetic field may result in a parallel or anti-parallel alignment of nuclear spins, (e.g., water proton spins), in the direction of the main magnetic field within the examination object. This results in a precession of the nuclear spins around the direction of the main magnetic field with a Larmor frequency. The Larmor frequency is dependent on a type of nucleus and on the magnetic flux density of the main magnetic field.

As the parallel alignment of the nuclear spins to the main magnetic field represents a thermal and energetic state of equilibrium, a parallel alignment of net magnetization to the main magnetic field frequently occurs. In this case, the net magnetization, hereinafter also referred to as magnetization, results as effective macroscopic magnetization of the individual magnetic dipole moments of the nuclear spins.

By a gradient coil unit, additional and spatially varying magnetic fields, (e.g., magnetic field gradients, hereinafter also referred to as gradients), may be output. A consequently position dependent Larmor frequency along the spatial dimension of the magnetic field gradients thus enables spatial encoding within an examination area. The spatial dimension of the magnetic field gradients may include a read-out direction and/or phase encoding direction and/or slice encoding direction, which directions are in particular orthogonal to one another. Hereinafter, magnetic field gradients along the read-out direction are referred to as read gradients. Furthermore, magnetic field gradients along the phase encoding direction are referred to as phase encoding gradients. In addition, magnetic field gradients along the slice encoding direction are referred to as slice encoding gradients. The differentiation described above, in particular the designation used hereinafter, of the magnetic field gradients into read gradients, phase encoding gradients, and slice encoding gradients indicates the spatial dimension of the respective magnetic field gradient.

Radiofrequency pulses (RF pulses), (e.g., excitation pulses or saturation pulses), may be output by a radiofrequency antenna unit. If an RF pulse is resonant with the Larmor frequency of the nuclear spins, excitation, (e.g., deflection), of the nuclear spins may take place from a state of equilibrium. The resulting transverse component of precession of net magnetization around the direction of the main magnetic field may lead to induction in the RF antenna unit. In this case, the transverse component of net magnetization decreases, (e.g., exponentially), with a transverse relaxation time constant. An MR signal, in particular a free induction decay (FID), may be detected by the RF antenna unit. In addition, longitudinal relaxation of net magnetization takes place back into the thermal state of equilibrium.

Magnetic resonance images (MR images) of the examination object may be reconstructed by the detected MR signals, which are in particular spatially encoded by the output of magnetic field gradients.

If several MR signals are read out after output of a single excitation pulse, the time course of a relaxation of the nuclear spins may be detected. The period of time between the output of the excitation pulse and the readout of an MR signal may be referred to as echo time (TE).

Frequently, the output of a plurality of gradients, (e.g., along different spatial dimensions), and of RF pulses is combined in a sequence, also called a pulse sequence or MR sequence. The sequence may also include a chronological sequence of readout windows (analog-to-digital conversion, ADC), within which a readout of MR signals is made possible.

When recording MR image data of an examination volume of an examination object, multi-slice recordings having a plurality of measurement slices are frequently carried out. Flow movements, (e.g., a pulsating blood flow), in particular between different layers of the recording, may lead to the transport, in particular an inflow, of magnetization from surrounding slices into a measurement slice. In particular, this may make it more difficult to identify areas of the examination volume contrasted by contrast agent, (e.g., a lesion). In order to suppress an MR signal of the inflowing magnetization, a predefined spatial area around the measurement slice, in particular outside the examination volume, may be saturated. For application in a multi-slice recording, because of the saturation frequently configured and/or allocated to each individual measurement slice (travelling sats), the increased measurement duration expenditure and the increased energy use, in particular the increased specific absorption rate (SAR), are disadvantageous.

SUMMARY AND DESCRIPTION

The task of the disclosure is therefore to enable a time-efficient recording of artefact-poor MR images.

The scope of the present disclosure is defined solely by the appended claims and is not affected to any degree by the statements within this summary. The present embodiments may obviate one or more of the drawbacks or limitations in the related art.

In a first aspect, the disclosure relates to a method for the saturation-prepared recording of MR image data. In act a), at least two measurement slices are established in an examination volume of an examination object. In this case, the examination volume has adjacent slices which each adjoin at least one of the at least two measurement slices. Furthermore, in act b.1), a saturation module including at least one saturation pulse for saturating a magnetization of the adjacent slices is output. Thereafter, in act c), an excitation pulse for exciting a magnetization of at least one of the at least two measurement slices is output. Furthermore, in act d), an MR signal of the examination volume is read out. In addition, the acts b.1) to d) are carried out until the magnetization of all of the at least two measurement slices has been excited. In further act e), the MR image data are reconstructed by the at least two measurement slices based on the MR signal. In addition, the MR image data is provided in act f).

The determination of the at least two measurement slices may advantageously include a spatial positioning of the at least two measurement slices in the examination volume, in particular based on an overview scan of the examination volume. The spatial positioning of the at least two measurement slices may have a spatial position and/or alignment of the at least two measurement slices with respect to the examination volume. In addition, the determination of the at least two measurement slices may include a specification of the at least one geometric parameter of the at least two measurement slices, (e.g., a spatial extension and/or a slice thickness and/or a spatial resolution). In addition, the determination may include a specification of a spatial positioning of the at least two measurement slices relative to one another and with respect to the examination volume. Furthermore, at least one geometric parameter of the at least two measurement slices may be predetermined, (e.g., an inter-slice distance and/or a slice thickness).

Furthermore, the at least two measurement slices may be determined manually and/or semi-automatically and/or automatically in the examination volume of the examination object. For example, the at least two measurement slices may be determined based on user input by an input unit. Furthermore, the user input may have information relating to at least one geometric parameter of the at least two measurement slices and/or the spatial positioning of the at least two measurement slices in the examination volume. In this case, the at least two measurement slices may be determined, (e.g., semi-automatically), at least partially based on the user input.

The at least two measurement slices may designate a spatial area within the examination volume, which spatial area is mapped in the MR image data to be recorded. The at least two measurement slices may advantageously be configured to be flat and have a slice plane along which slice plane the at least two measurement slices are spatially resolved. The at least two measurement slices may be arranged in the examination volume parallel to one another and/or along a spatial dimension, which spatial dimension has a common, in particular right, angle with respect to the respective slice plane. The slice planes of the at least two measurement slices may in particular each be a center plane of the associated measurement slice.

Furthermore, the examination volume may designate a spatial, in particular three-dimensional, section of the examination object. The examination volume may advantageously be greater along at least one spatial dimension than the at least two measurement slices. The examination object may be a human and/or animal patient and/or an examination phantom.

Furthermore, the examination volume may advantageously have at least three adjacent slices which, in particular directly, adjoin the at least two measurement slices. The adjacent slices may advantageously be arranged in the spatial areas of the examination volume, in which spatial areas no measurement slice is arranged. Consequently, the adjacent slices and the at least two measurement slices may spatially fill the examination volume, in particular completely. The adjacent slices may each have a slice plane, in particular analogously to the at least two measurement slices. The slice planes of the adjacent slices may each be a center plane of the associated adjacent slice.

The examination volume may advantageously have one adjacent slice more than measurement slices that were determined in act a). The adjacent slices may surround the determined measurement slices along the spatial dimension, which spatial dimension has a common, in particular right, angle with respect to the respective slice plane of the at least two measurement slices. Furthermore, the slice thickness of the adjacent slices may correspond to the slice distance between, in each case, two of the at least two measurement slices. In this case, two of the adjacent slices, which each adjoin precisely one measurement slice, may be configured as edge slices of the examination volume. Furthermore, the remaining adjacent slices which adjoin two different measurement slices in each case, may be configured as intermediate slices of the examination volume. Consequently, each of the at least two measurement slices may adjoin precisely two different adjacent slices in each case. Analogously to the at least two measurement slices, the adjacent slices in the examination volume may be arranged parallel to one another and/or along the spatial dimension, which spatial dimension has a common, in particular right, angle with respect to the respective slice plane. The adjacent slices may advantageously have an identical or different spatial extension and/or resolution with respect to the at least two measurement slices along the respective slice plane of the adjacent slices.

In act b), the saturation module including the at least one saturation pulse may be output to saturate the magnetization of the adjacent slices, wherein the at least one saturation pulse is formed by an RF pulse. In this case, the saturation module may describe an MR sequence section which is configured to saturate the magnetization of the adjacent slices. The saturation module, in particular the at least one saturation pulse, may cause a deflection of the magnetization of the adjacent slices, in particular out of the state of equilibrium and/or into a transverse plane. Furthermore, the saturation module, in particular the at least one saturation pulse, may be configured to generate an, in particular maximum, phase dispersion of the magnetization within the transverse plane. This may provide that the magnetization of the adjacent slices is saturated after the output of the saturation module. In this case, the at least one saturation pulse may be configured to saturate a predetermined resonance frequency range corresponding to the adjacent slices, in particular selectively and/or unselectively. For, (e.g., simultaneous), saturation of the adjacent slices, the at least one saturation pulse may be configured as a multi-band pulse, wherein in each case a saturation band, (e.g., a frequency band for saturation), corresponds to one of the adjacent slices.

In act c), an excitation pulse for excitation of the magnetization of at least one, in particular all, of the at least two measurement slices may be output, the excitation pulse being formed by an RF pulse. The excitation pulse may cause an, in particular selective, deflection of the magnetization of at least one of the at least two measurement slices, in particular out of the state of equilibrium, around a predetermined flip angle. The excitation pulse may advantageously be configured as a multi-band pulse for, in particular simultaneous, excitation of at least one of the at least two measurement slices. If acts b.1) to d) are repeated, the magnetization of at least one measurement slice, in particular not all the measurement slices, of the at least two measurement slices may be excited by the output of the excitation pulse. Advantageously, the excitation pulse may be adapted during each execution of acts b.1) to d) in such a way that the at least one measurement slice whose magnetization is excited is different from the previous measurement slices. Furthermore, a number of the at least one of the at least two measurement slices when executing acts b.1) to d) may be the same or different from the respective previous execution of acts b.1) to d). If necessary, act c) may include an output of at least one further excitation pulse for exciting a magnetization of at least one of the at least two measurement slices of the respective execution of acts b.1) to d). Thus, the excitation pulse may be configured to excite the magnetization of a single or all of the at least one of the at least two measurement slices.

Advantageously, acts b.1) to d) may be carried out, in particular repeatedly, until the magnetization of all of the at least two measurement slices has been excited in act b.1). If the excitation pulse in act b.1) is configured to excite all of the at least two measurement slices, a single execution of acts b.1) to d) may suffice. Furthermore, act b.1) may be carried out repeatedly.

In act d), in each execution of acts b.1) to d), in each case, one MR signal of the examination volume may be read out, hereinafter also referred to as the at least one MR signal. The readout of the respective MR signal may include an output of an MR sequence section for reading out the respective MR signal. The MR sequence section may include an output of further RF pulses, in particular excitation pulses and/or saturation pulses, and/or an output of magnetic field gradients, (e.g., read gradients and/or phase encoding gradients and/or slice encoding gradients and/or spoiler gradients). As a result, the respective MR signal, in particular in the k-space, may be spatially encoded. The MR sequence section for reading out the respective MR signal may be specified, for example, according to a gradient echo sequence (GRE) and/or a spin echo sequence (SE).

Because each execution of acts b.1) to d) the magnetization of the adjacent slices is saturated by the output of the saturation module in act b.1), a pseudo-continuous saturation of the magnetization of the adjacent slices may advantageously be achieved. As a result, structural specifications of the magnetic resonance system, (e.g., a maximum pulse duration), and/or safety-relevant limit values, (e.g., a specific absorption rate (SAR)), may advantageously be maintained. In addition, a high degree of saturation efficiency within the adjacent slices may thereby be achieved. The magnetization of the adjacent slices may be deflected out of the state of equilibrium, in particular after a predefined number of executions of acts b.1) to d), into the transverse plane.

In this way, a particularly low-energy and at the same time efficient saturation of the magnetization of the adjacent slices may be made possible.

As a result of the selective saturation of the adjacent slices in act b.1) and the selective excitation of at least one of the at least two measurement slices in act c), it may be advantageously achieved that the respective MR signal predominantly has signal components of at least one of the at least two measurement slices. Furthermore, the simultaneous saturation of the adjacent slices and/or the simultaneous excitation of at least one of the at least two measurement slices makes it possible to reduce the measurement duration.

The reconstruction of the MR image data from the at least two measurement slices in act e) may advantageously include an inverse Fourier transform of the at least one MR signal. As a result, the at least one MR signal may be converted from the k-space into the MR image data in the image space.

The provision of the MR image data in act f) may include storage on a computer-readable storage medium and/or display on a display unit and/or transmission to a processing unit. In particular, a graphic representation of the MR image data may be displayed on the display unit.

The proposed method enables particularly thorough and simultaneously time-efficient suppression, in particular saturation, of signal components outside the at least two measurement slices. As a result, particularly artefact-poor MR image data from the recorded MR signal may be reconstructed and provided.

In a further advantageous embodiment of the proposed method, the saturation module may be configured to saturate magnetization of a blood flow within the adjacent slices.

If the examination volume has at least one vessel section, (e.g., one blood vessel), a flow movement, (e.g., a blood flow), may occur at least partially within the examination volume. The flow movement may occur between the at least two measurement slices and at least one of the adjacent slices. This may result in a transport, in particular an inflow, of magnetization of one of the adjacent slices into one of the at least two measurement slices. Due to the fact that the flow movement, transports (e.g., constantly) magnetization between the adjacent slices and the at least two measurement slices, the inflowing magnetization of the adjacent slices may lead to artefacts, (e.g., a flow artefact), in the MR signal of the at least two measurement slices.

The saturation module may advantageously be configured to saturate the magnetization of the blood flow within the adjacent slices, which magnetization may be transported into the at least two measurement slices. In contrast to a sequential saturation of the magnetization of individual adjacent slices, the proposed method enables a particularly time-efficient, in particular simultaneous, saturation of all the adjacent slices. As the blood flow, in particular the transport of the magnetization from the adjacent slices, is time-dependent, a particularly effective reduction of flow artefacts in the MR signal of the at least two measurement slices and consequently also in the MR image data may be achieved.

In a further advantageous embodiment of the proposed method, acts a) to f) may be carried out repeatedly. The previous adjacent slices in act a) may be at least partially defined as measurement slices. This enables imaging of the examination volume in the MR image data, which is complete except for the edge slices. Advantageously, the magnetization of the edge slices may furthermore be at least partially saturated by the saturation module in act b.1) in order to avoid flow artefacts by transporting this magnetization into the respective adjacent measurement slice.

Advantageously, the previous adjacent slices, which adjoin two measurement slices in each case, (e.g., the intermediate slices), may be determined at least partially, (e.g., completely), as measurement slices in act a) for the respective subsequent repetition. If the intermediate slices have a slice thickness which differs from the slice thickness of the at least two measurement slices, it may be advantageous to determine these intermediate slices only partially, in particular proportionally, as measurement slices for the respective subsequent repetition. In particular, in each case a portion of a previous intermediate slice may be defined as the measurement slice, which portion has the same slice thickness as the previous measurement slices. In this way, it may be advantageously achieved that the previous excitation pulse, displaced by a defined distance along the spatial dimension, along which spatial dimension the at least two measurement slices are lined up, may be used to excite the magnetization of the measurement slices in the respective subsequent repetition. Analogously, the previous saturation module, displaced by the defined distance along the spatial dimension, along which spatial dimension the at least two measurement slices are lined up, may be used to saturate the magnetization of the adjacent slices in the respective subsequent repetition.

This makes it possible to map the examination volume by reading out at least one MR signal for each repetition of acts a) to f), the at least one MR signal corresponding to a package of measurement slices (slice package). Furthermore, flow artefacts may be reduced particularly efficiently by saturating the magnetization of the adjacent slices in the repetitions of acts a) to f).

In a further advantageous embodiment of the proposed method, the saturation module, in particular the at least one saturation pulse, may have a spatial saturation profile determined as a function of the at least two measurement slices. The at least two measurement slices, and in particular also the adjacent slices, may have at least partially different slice thicknesses and/or slice distances from one another. The saturation module, in particular the spatial saturation profile, may be determined as a function of the slice thickness and/or the slice distance of the at least two measurement slices. The saturation profile may specify a spatial distribution of saturated magnetization which is to be achieved by the output of the saturation module in act b.1). Advantageously, the spatial saturation profile may be specified in such a way that the magnetization of the adjacent slices may be selectively almost completely saturated by the output of the saturation module. Advantageously, the magnetization of the at least two measurement slices may remain virtually unaffected and/or unchanged by the output of the saturation module.

This enables a particularly precise saturation of the magnetization of the adjacent slices and thus suppression of possible flow artefacts in the MR image data.

If acts a) to f) are carried out repeatedly, the spatial saturation profile may be advantageously determined and/or adapted as a function of the adjacent slices to the measurement slices determined in act a) of the respective repetition. This is advantageous in particular when there is a change in the slice thickness and/or the slice distance of the measurement slices between, in particular successive, repetitions of acts a) to f).

If the slice distance and/or the slice thickness between, in particular successive, repetitions of acts a) to f) remains unchanged, the previous spatial saturation profile, displaced by the defined distance along the spatial dimension along which spatial dimension the at least two measurement slices are lined up, may be specified for the saturation module in the respective subsequent repetition of acts a) to f).

Spatially modulated preparation (SPAMP) may be used to achieve the saturation profile, which functions similarly to spatial modulation of magnetization (SPAMM) in myocardial imaging. Advantageously, spatially modulated preparation may be configured to imprint a saturation pattern according to the predefined saturation profile onto the at least one MR signal, (e.g., the MR image data), the saturation pattern having parallel stripes, (e.g., corresponding to the adjacent slices). The saturation profile or saturation pattern generated in the process may follow a periodic function which is incorporated into the adjacent slices. In this case, the at least two measurement slices are advantageously omitted from the saturation profile with respect to the magnetization to be saturated.

In a further advantageous embodiment of the proposed method, the excitation pulse may have a spatial excitation profile which is determined as a function of at least one of the at least two measurement slices.

The at least two measurement slices may have at least partially different slice thicknesses and/or slice distances from one another. The excitation pulse, in particular the spatial excitation profile, may be determined as a function of the slice thickness and/or the slice distances of at least one of the at least two measurement slices. The excitation profile may specify a spatial distribution of excited magnetization which is to be achieved by the output of the excitation pulse in act c). Advantageously, the spatial excitation profile may be specified in such a way that the magnetization of at least one of the at least two measurement slices may be selectively excited by the output of the excitation pulse. Advantageously, the magnetization of the adjacent slices and/or the remaining measurement slices may remain virtually unaffected and/or unchanged by the output of the excitation pulse. In particular, for each execution of acts b.1) to d), a spatial excitation profile configured to at least one of the at least two measurement slices may be specified for the excitation pulse.

In this way, a particularly precise excitation of the magnetization of at least one of the at least two measurement slices may be made possible for the subsequent readout of the MR signal.

If acts a) to f) are carried out repeatedly, the spatial excitation profile may be advantageously determined and/or adapted as a function of the measurement slices determined in act a) of the respective repetition of acts a) to f). This is advantageous in particular when there is a change in the slice thickness and/or the slice distance of the measurement slices between, in particular successive, repetitions of acts a) to f).

If the slice distance and/or the slice thickness between, in particular successive, repetitions of acts a) to f) remains unchanged, the previous spatial excitation profile, displaced by the defined distance along the spatial dimension along which spatial dimension the at least two measurement slices are lined up, may be specified for the excitation pulse in the respective subsequent repetition of acts a) to f).

In a further advantageous embodiment of the proposed method, the saturation profile, and the excitation profile may be determined as a function of one another in such a way that a predefined spatial signal profile for the at least one MR signal is achieved at least for the adjacent slices. In order to determine the saturation profile and the excitation profile, a mutual interaction between the output of the saturation module and the excitation pulse may be taken into account in such a way that, when the MR signal is read out in act d), the predefined spatial signal profile may be achieved at least for the adjacent slices, in particular also for at least one of the at least two measurement slices. Advantageously, the spatial signal profile may specify a spatial signal distribution which is not to be exceeded in spatial areas of the adjacent slices. The spatial signal profile may in particular describe a combination, in particular superimposition, of the spatial saturation profile and the spatial excitation profile, in particular taking into account relaxation effects of the magnetization until the MR signal is read out in act d).

Furthermore, the specification of the spatial signal profile, in particular at border areas between a measurement slice and an adjacent slice, enables the sharpest and most precise possible delimitation between saturated and excited magnetization of the respective slice.

In a further advantageous embodiment of the proposed method, the saturation module may also include at least one tagging gradient. The at least one tagging gradient may be configured as a read gradient and/or phase encoding gradient and/or a slice encoding gradient. For this purpose, the tagging gradient may be output along the read-out direction and/or phase encoding direction and/or slice encoding direction. Furthermore, the at least one saturation pulse may be configured for the unselective saturation of the magnetization of the examination volume. In this case, the at least one tagging gradient may be configured for the selection, (e.g., structuring), of the saturation caused by the at least one, (e.g., unselective), saturation pulse in the examination volume. The at least one tagging gradient may advantageously be configured to generate a saturation profile, in particular a grid-shaped saturation profile, corresponding to the adjacent slices in the examination volume. In an exemplary embodiment, the saturation module may be similar to a Delay Alternating with Nutation for Tailored Excitation (DANTE). In this case, the saturation module may have at least two, (e.g., identical), saturation pulses, which may be configured as short, hard RF pulses. In addition, the at least one tagging gradient may be output temporally between and/or simultaneously to the at least two saturation pulses.

The at least one tagging gradient enables selective saturation of the adjacent slices, in particular in conjunction with the at least one saturation pulse. This enables simple implementation of the saturation module.

In a further advantageous embodiment of the proposed method, the saturation module, in particular the at least one saturation pulse and/or the at least one tagging gradient, and/or the excitation pulse may be determined as a function of a tissue parameter and/or a blood flow parameter and/or a relaxation parameter of the examination object.

The tissue parameter may include a susceptibility parameter and/or a physiological parameter and/or information relating to the saturation transfer rate of at least one tissue of the examination object, in particular of the examination volume. Furthermore, the blood flow parameter may include information relating to the gas content, in particular oxygen content (blood oxygenation), and/or information relating to the flow rate and/or information relating to the direction of flow and/or information relating to the volume flow. Furthermore, the relaxation parameter may include information relating to the longitudinal and/or transverse relaxation rate of at least one tissue and/or blood flow of the examination object. Advantageously, the parameters described above may be spatially resolved. In this way, a particularly precise determination of the saturation module and/or of the excitation pulse, in particular taking into account time-sensitive effects, may be made possible. Determining the saturation module and/or the excitation pulse as a function of the tissue parameter and/or of the blood flow parameter and/or of the relaxation parameter may in particular include adapting a pulse duration and/or a pulse amplitude and/or a pulse phase. Advantageously, an interpulse-delay, in particular of the at least one saturation pulse and/or of the at least one tagging gradient, may be specified as a function of the tissue parameter and/or of the blood flow parameter and/or of the relaxation parameter of the examination object.

The parameters described above may be determined based on a received tissue map of the examination object. Alternatively or in addition, the parameters described above may be specified based on a user input, in particular a recording protocol. A sufficient saturation of the magnetization of the adjacent slices and/or excitation of the magnetization of the at least two measurement slices may thereby advantageously be made possible.

In a further advantageous embodiment of the proposed method, the saturation module may have an effective flip angle of less than 90°. If acts b.1) to d) are carried out several times in order to excite the magnetization of all of the at least two measurement slices, the magnetization of the adjacent slices may be saturated pseudo-continuously by the saturation pulse. In this case, a comparatively short repetition time (TR) may be specified for the, in particular repeated, execution of acts b.1) to d), in particular with respect to a longitudinal relaxation time (T1). As a result, the saturation of the magnetization of the adjacent slices during the repeated output of the at least one saturation pulse may advantageously increase with each execution of acts b.1) to d). After a predetermined number of, in particular repeated, executions of acts b.1) to d), a steady state with regard to the saturation of the magnetization of the adjacent slices may occur.

The effective flip angle may denote a flip angle, in particular a deflection angle, of the magnetization of the adjacent slices, in particular unique, output of the saturation module in act b.1). The effective flip angle of the saturation module may be the same as or different from a flip angle of the at least one saturation pulse. In addition, the effective flip angle of the saturation module may advantageously be specified as a function of the tissue parameter and/or of the blood flow parameter and/or of the relaxation parameter of the examination object.

As a result, structural specifications of the magnetic resonance system, (e.g., a maximum pulse duration), and/or safety-relevant limit values, (e.g., a specific absorption rate (SAR)), may advantageously be maintained. Furthermore, a high degree of saturation efficiency within the adjacent slices may be achieved. In addition, a total measurement duration for recording the MR image data may be advantageously reduced.

In a further advantageous embodiment of the proposed method, it may further include act b.2), wherein at least one spoiler gradient is output in act b.2). Act b.2) may advantageously be carried out after act b.1) and before act c). Furthermore, the at least one spoiler gradient may be configured to reduce a phase coherence of the magnetization of the adjacent slices in the transverse plane. Furthermore, the at least one spoiler gradient may be configured as a read gradient, phase encoding gradient, or slice encoding gradient. In addition, in act b.2), at least one further spoiler gradient may be output along at least one of the remaining spatial dimensions. The at least one spoiler gradient and the at least one further spoiler gradient may be output in particular simultaneously. In particular, the at least one spoiler gradient may be output along the slice encoding direction and the at least one further spoiler gradient may be output along the read-out direction and/or the phase encoding direction. The at least one further spoiler gradient may be configured analogously to the at least one spoiler gradient in order to reduce the phase coherence of the magnetization of the adjacent slices in the transverse plane. Advantageously, acts b.1) and b.2) may be carried out one after the other, in particular in any order, and/or simultaneously and/or in each case repeatedly.

This enables improved, in particular selective, saturation of the magnetization of the adjacent slices, in particular before the excitation of the magnetization of at least one of the at least two measurement slices in act c).

In a further advantageous embodiment of the proposed method, acts b.1) and b.2) may be carried out repeatedly. Depending on temporal parameters of the proposed method, (e.g., the repetition time of acts b.1) to d) and/or the pulse duration of the at least one saturation pulse and/or a duration of the at least one tagging gradient and/or at least one relaxation parameter of the examination object), a single execution of acts b.1) and b.2) may be insufficient for an, in particular almost complete, saturation of the magnetization of the adjacent slices. Advantageously, the, in particular selective, saturation of the magnetization of the adjacent slices may be improved by the repeated execution of acts b.1) and b.2). This is particularly advantageous in the case of a short longitudinal relaxation time (T1) of the area of the examination object to be saturated, in particular with regard to the repetition time of acts b.1) to d). Furthermore, the temporal parameters of acts b.1) and b.2), (e.g., the pulse duration of the at least one saturation pulse and/or a duration of the at least one tagging gradient and/or a repetition time of acts b.1) and b.2) and/or a duration of the spoiler gradient), may be predefined as a function of the remaining temporal parameters of the proposed method and/or as a function of the tissue parameter and/or of the blood flow parameter and/or of the relaxation parameter of the examination object. In this way, a particularly reliable saturation of the magnetization of the adjacent slices may be provided.

In a second aspect, the disclosure relates to a magnetic resonance system which is configured to execute a proposed method for the saturation-prepared recording of MR image data. The magnetic resonance system may include an RF processing unit, a gradient control unit, a sequence control unit, and a processing unit. In particular, the components of the magnetic resonance system may be configured to execute the individual method acts of a proposed method for the saturation-prepared recording of MR image data.

For this purpose, the magnetic resonance system may use the sequence control unit to specify an MR sequence for the saturation-prepared recording of MR image data. Furthermore, the MR sequence may include an output of RF pulses, in particular excitation pulses and/or saturation pulses, wherein the RF pulses may be output by the RF processing unit. In addition, the MR sequence may include an output of magnetic field gradients, (e.g., read gradients and/or phase encoding gradients and/or slice encoding gradients and/or spoiler gradients), wherein the magnetic field gradients may be output by the gradient control unit. In particular, the MR sequence may specify a scan of the k-space for recording the at least one MR signal. The RF processing unit may also be configured to detect the at least one MR signal and to provide said at least one MR signal to the processing unit. The processing unit may be configured to reconstruct and/or provide the MR image data from the at least two measurement slices based on the at least one MR signal.

In addition, the magnetic resonance system may have an input unit, (e.g., a keyboard and/or a pointing unit), which is configured to record a user input. The processing unit may be configured to define the at least two measurement slices in the examination volume based on the user input.

Furthermore, the magnetic resonance system may include a display unit, (e.g., a display and/or a monitor and/or an LED display), which is configured to display information and/or graphic representations of information of the magnetic resonance system and/or of further components of the magnetic resonance system and/or the MR image data.

The advantages of the proposed magnetic resonance system may correspond to the advantages of the proposed method for the saturation-prepared recording of MR image data. Features, advantages, or alternative embodiments mentioned herein may also be transferred to the other claimed subjects, and vice versa.

In a third aspect, the disclosure relates to a computer program product having a computer program which may be loaded directly into a memory of a processing unit, having program sections in order to carry out all the acts of the proposed method for the saturation-prepared recording of MR image data when the program sections are executed by the processing unit. The computer program product may include software having a source code which has yet to be compiled and linked or which only has to be interpreted, or an executable software code which only needs to be loaded into the processing unit for execution. By the computer program product, the method for the saturation-prepared recording of MR image data may be carried out in a rapid, identically repeatable, and robust manner by a processing unit. The computer program product is configured in such a manner that it may execute the method acts by the processing unit.

The computer program product is stored, for example, on a computer-readable storage medium or stored on a network or server, from where it may be loaded into the processor of a processing unit which may be directly connected to the processing unit or may be configured as part of the processing unit. Furthermore, control information of the computer program product may be stored on an electronically readable data carrier. The control information of the electronically readable data carriers may be configured in such a way that, when the data carrier is used in a processing unit, it performs a method as described herein. Examples of electronically readable data carriers are a DVD, a magnetic tape, or a USB stick on which electronically readable control information, in particular software, is stored. When this control information is read from the data carrier and stored in a processing unit, all of the embodiments of the method described above may be performed.

The disclosure may also proceed from a computer-readable storage medium and/or electronically readable data carrier on which program sections which may be read and executed by a processing unit are stored in order to carry out all the acts of the method for the saturation-prepared recording of MR image data when the program sections are executed by the processing unit.

A largely software-based implementation has the advantage that processing units already used previously may be retrofitted in a simple manner by a software update in order to operate in the manner disclosed herein. In addition to the computer program, such a computer program product may optionally include additional elements such as, for example, documentation and/or additional components, as well as hardware components such as hardware keys (e.g., dongles, etc.) for using the software.

BRIEF DESCRIPTION OF THE DRAWINGS

Exemplary embodiments of the disclosure are shown in the drawings and are described in more detail hereinafter. In different figures, the same reference characters are used for the same features. The drawings show.

DETAILED DESCRIPTION

Figure 1:
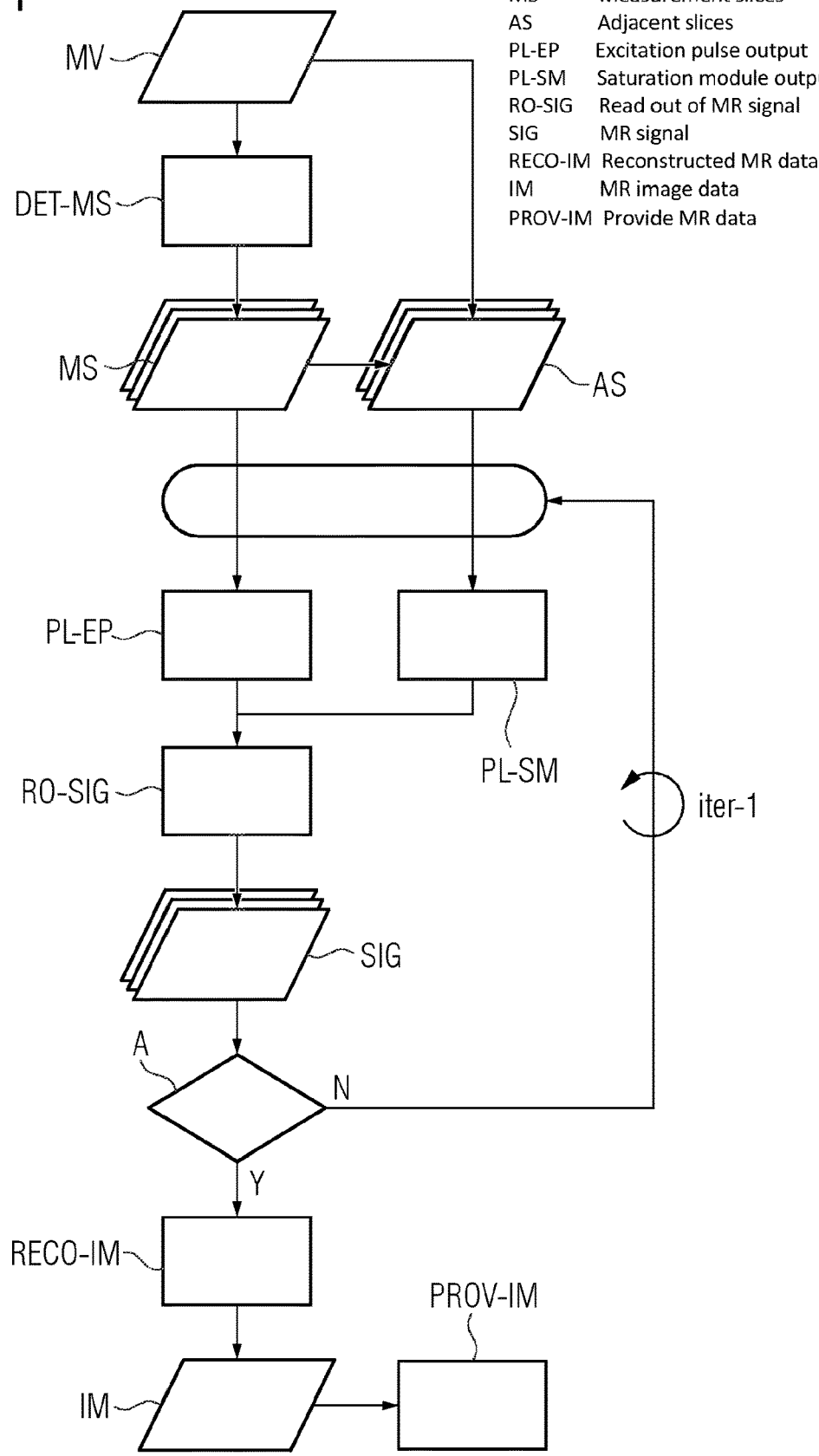
FIGS. 1 to 3 depict diagrammatic views of various embodiments of a proposed method for the saturation-prepared recording of MR image data.

FIG. 1 depicts a diagrammatic view of an embodiment of a proposed method for the saturation-prepared recording of MR image data. In act a), at least two measurement slices MS are determined in an examination volume MV of an examination object, DET-MS. The examination volume MV may have adjacent slices AS, which each adjoin at least one of the at least two measurement slices MS. In act b.1), a saturation module including at least one saturation pulse for saturating a magnetization of the adjacent slices AS may be output PL-SM. Furthermore, in act c), an excitation pulse for exciting a magnetization of at least one of the at least two measurement slices MS may be output PL-EP. Hereinafter, in act d), an MR signal SIG of the examination volume MV may be read out RO-SIG. Acts b.1) to d) may be carried out, in particular repeated, iter-1, until the termination condition A occurs. The termination condition A may check whether the magnetization of all of the at least two measurement slices MS has been excited.

The excitation pulse may be configured to excite the magnetization of all of the at least two measurement slices MS, in particular simultaneously. In this case, a single execution of acts b.1) to d) may suffice for the recording of the MR signal SIG to all of the at least two measurement slices MS. Alternatively, acts b.1) to d) may be carried out, in particular repeated, iter-1, until MR signals SIG have been recorded for all of the at least two measurement slices MS. Advantageously, at least one of the at least two measurement slices MS may be specified in each subsequent execution of acts b.1) to d) iter-1 in such a way that the magnetization thereof has not yet been excited.

After the occurrence Y of the termination condition A, the MR image data IM may be reconstructed by the at least two measurement slices MS based on the at least one MR signal SIG in act e) RECO-IM. Hereinafter, the MR image data IM may be provided in act f) PROV-IM.

The saturation module may be configured in particular to saturate magnetization of a blood flow within the adjacent slices AS. Furthermore, the output of the saturation module SM may be referred to in act b.1) as a saturation preparation.

Furthermore, the saturation module, in particular of the at least one saturation pulse, and/or the excitation pulse may be determined as a function of a tissue parameter and/or a blood flow parameter and/or a relaxation parameter of the examination object.

Figure 2:
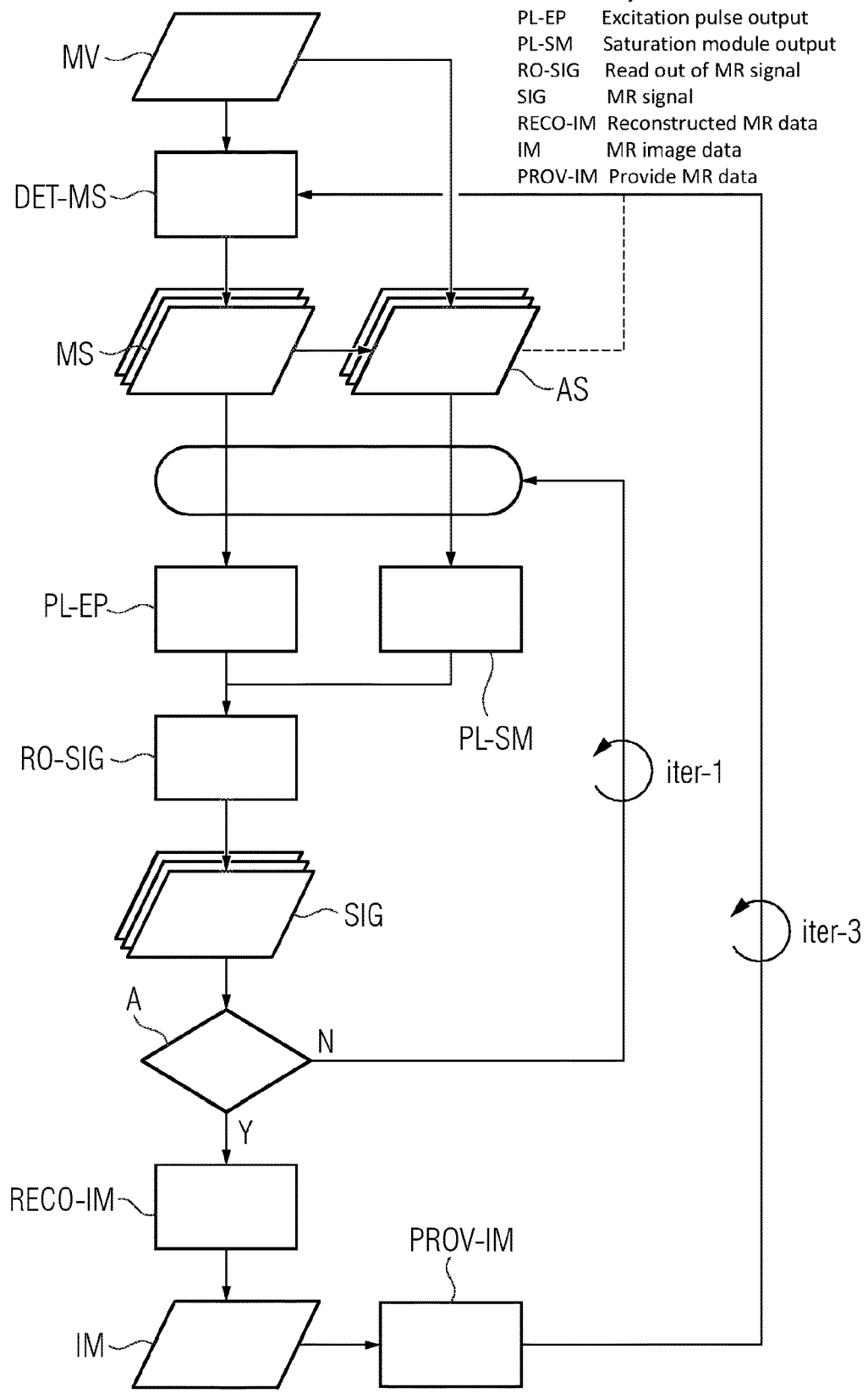

FIG. 2 depicts a further advantageous embodiment of the proposed method for the saturation-prepared recording of MR image data IM. In this case, acts a) to f) may be carried out repeatedly iter-3. In this case, the previous adjacent slices AS in act a) may be at least partially defined as measurement slices MS DET-MS.

Figure 3:
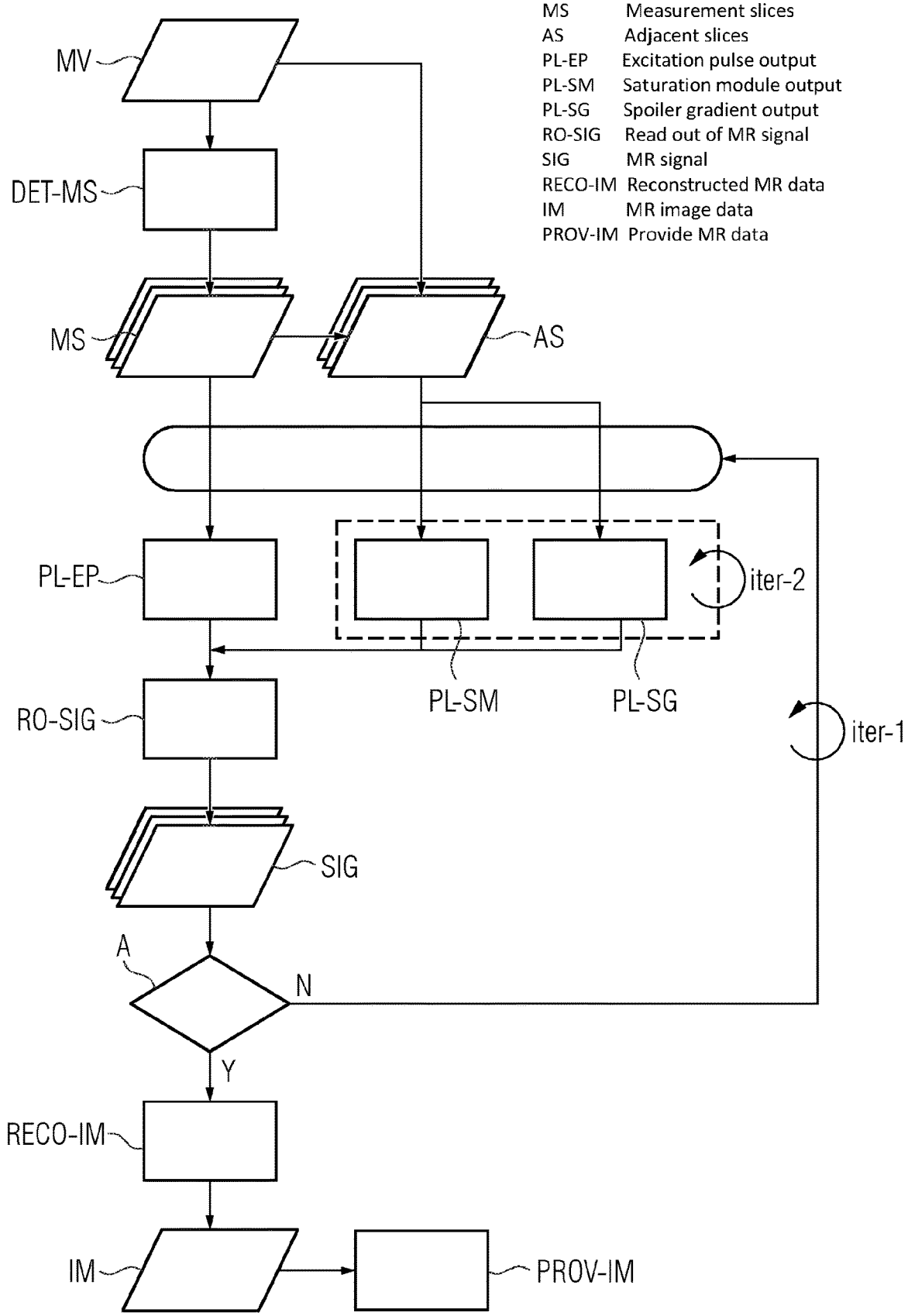

FIG. 3 depicts a further advantageous embodiment of the proposed method for the saturation-prepared recording of MR image data IM. The method may further include act b.2), wherein at least one spoiler gradient is output PL-SG. Furthermore, acts b.1) and/or b.2) may be carried out repeatedly iter-2.

Figure 4:
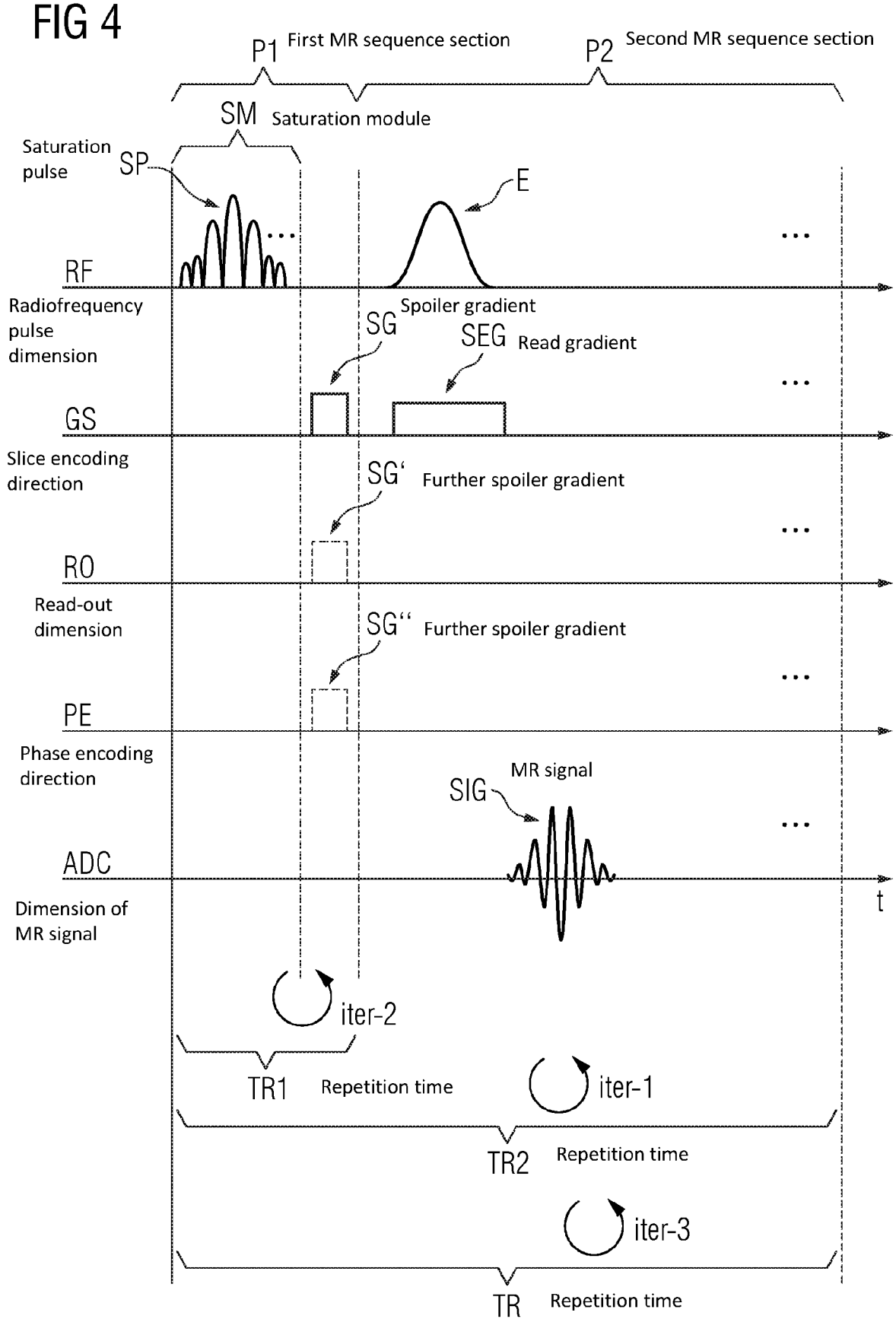
FIGS. 4 and 5 depict diagrammatic views of various exemplary MR sequences for the saturation-prepared recording of MR image data.
Figure 5:
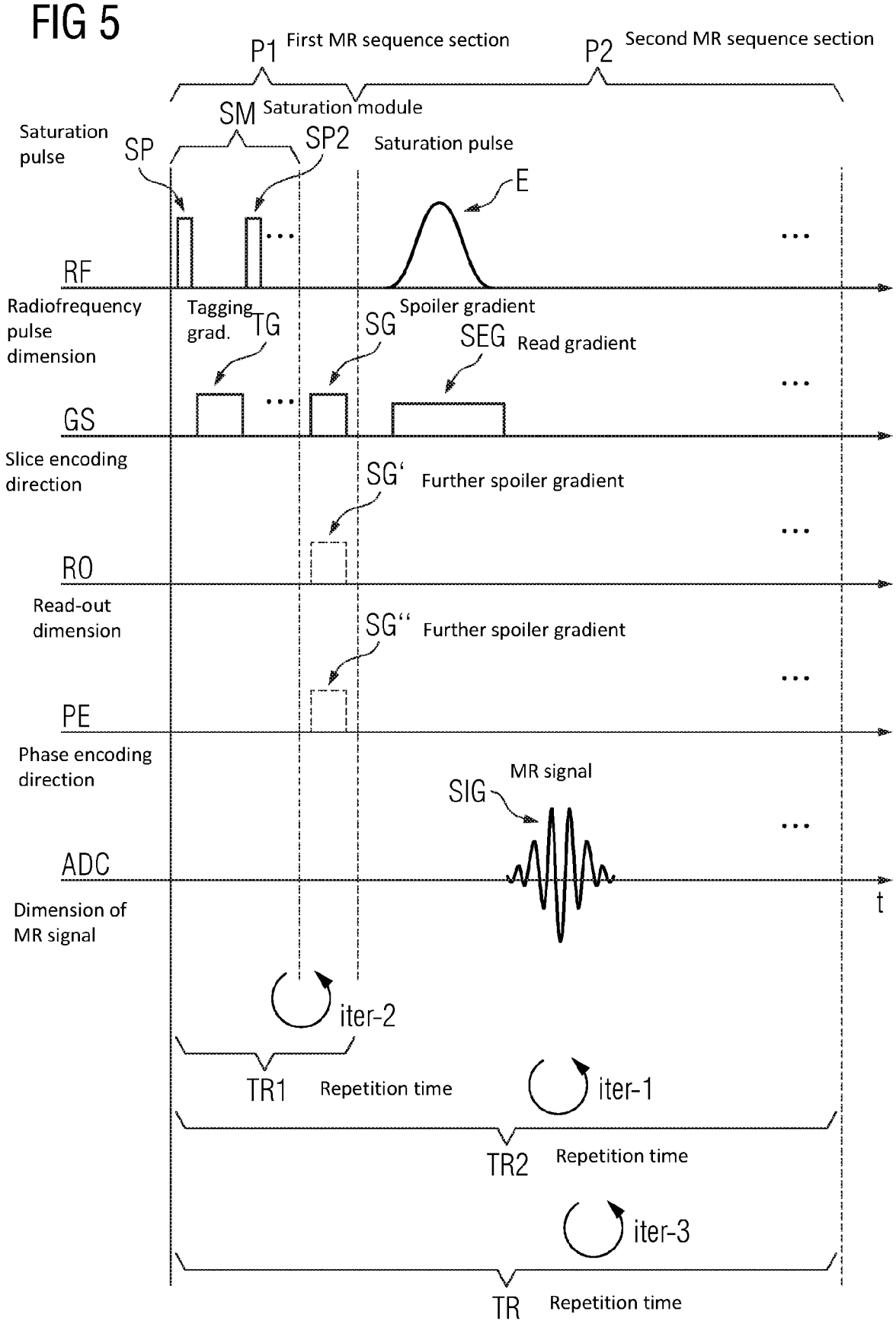

FIGS. 4 and 5 depict diagrammatic views of various exemplary MR sequences for the saturation-prepared recording of MR image data IM. A course of the output of RF pulses, magnetic field gradients and the reception of the at least one MR signal along the different dimensions is shown in the time course t. Here, RF denotes the dimension of the RF pulses, RO denotes a read-out dimension for outputting read gradients, PE denotes a phase encoding direction for outputting phase encoding gradients and GSM a slice encoding direction for outputting slice encoding gradients. Furthermore, ADC denotes a dimension of the at least one MR signal. The MR sequence may have at least one first MR sequence section P1 and at least one second MR sequence section P2, wherein the first MR sequence section P1 includes the at least one saturation module SM.

The acts b.1), in particular the output of the saturation module SM including the at least one saturation pulse SP, and b.2), including the output of at least one spoiler gradient SG, may be executed within the first MR sequence section P1. The saturation module SM may have an effective flip angle of less than 90°. Furthermore, the acts c), including the output of the at least one excitation pulse EP, and d), including the readout of the MR signal SIG of the examination volume MV, may be carried out within the second MR sequence section P2. The at least one spoiler gradient SG may advantageously be configured to reduce a phase coherence of the magnetization of the adjacent slices AS in the transverse plane. In addition, the at least one spoiler gradient SG may be configured as a slice encoding gradient. Advantageously, acts b.1) and b.2) may be carried out one after the other in any order and/or simultaneously. Furthermore, in act b.2), at least one further spoiler gradient, which may be configured as a read gradient SG' and/or a phase encoding gradient SG", may be output, in particular at the same time as the at least one spoiler gradient SG. The at least one further spoiler gradient SG', SG" may be configured analogously to the at least one spoiler gradient SG to reduce the phase coherence of the magnetization of the adjacent slices AS in the transverse plane.

The second MR sequence section P2 may include an output of further RF pulses, in particular excitation pulses and/or saturation pulses, and/or an output of magnetic field gradients, (e.g., read gradients SAG and/or phase encoding gradients and/or slice encoding gradients and/or spoiler gradients). As a result, the respective MR signal SIG, in particular in the k-space, may be spatially encoded. The second MR sequence section P2 for reading out the respective MR signal SIG may be specified, for example, according to a gradient echo sequence (GRE) and/or a spin echo sequence (SE).

In a repeated execution iter-1 of acts b.1) to d) for the at least two measurement slices MS, the magnetization of the adjacent slices AS may be saturated pseudo-continuously by the saturation module SM, in particular of the at least one saturation pulse SP, and/or of the at least one spoiler gradient SG and/or of the at least one further spoiler gradient SG' and/or SG". In this case, for the repeated execution iter-1 of acts b.1) to d), a repetition time TRY which is comparatively short, in particular with respect to a longitudinal relaxation time, may be predefined, in particular for the execution of acts b.1) to d). As a result, the saturation of the magnetization of the adjacent slices AS during the repeated output of the saturation module SM may advantageously increase with each execution of acts b.1) to d) iter-1.

Furthermore, acts a) to f), in particular of the at least one first MR sequence section P1 and of the at least one second MR sequence section P2, may be carried out repeatedly iter-3. The acts a) to f), in particular including all repetitions iter-1 of acts b.1) to d) to be carried out for the excitation of all of the at least two measurement slices MS, may have a repetition time TRY, wherein acts a), e) and f) advantageously do not contribute to the repetition time TR.

FIG. 4 depicts an exemplary embodiment, the at least one saturation pulse SP being configured for the simultaneous saturation of the magnetization of the adjacent slices AS.

FIG. 5 depicts a further exemplary embodiment, the saturation module SM furthermore including a tagging gradient TG. The at least one tagging gradient TG may be configured as a read gradient and/or phase encoding gradient and/or a slice encoding gradient. In the exemplary embodiment shown here, the tagging gradient TG may be output along the slice encoding direction GS. The saturation module SM may be configured similarly to a Delay Alternating with Nutation for Tailored Excitation (DANTE) preparation. In this case, the saturation module SM may have two, in particular identically configured, saturation pulses SP and SP2, which may be configured as short hard RF pulses. In addition, the tagging gradient TG may be output between and/or at the same time as the two saturation pulses SP and SP2. The saturation pulses SP and SP2 may be configured for the unselective saturation of the magnetization of the examination volume MV. In addition, the tagging gradient TG may be configured for the selection, in particular structuring, of the saturation in the examination volume MV caused by the saturation pulses SP and SP2. The tagging gradient TG may advantageously be configured to generate a saturation profile, in particular a grid-shaped saturation profile, corresponding to the adjacent slices AS in the examination volume MV.

Furthermore, the temporal parameters of acts b.1) and b.2), in particular the pulse duration of the at least one saturation pulse SP and/or a duration of the at least one tagging gradient TG and/or a repetition time TR1 of acts b.1) and b.2) and/or a duration of the at least one spoiler gradient SG and/or a duration of the at least one further spoiler gradient SG', SG", may be predefined as a function of the remaining temporal parameters of the proposed method and/or as a function of the tissue parameter and/or the blood flow parameter and/or the relaxation parameter of the examination object.

Figure 6:
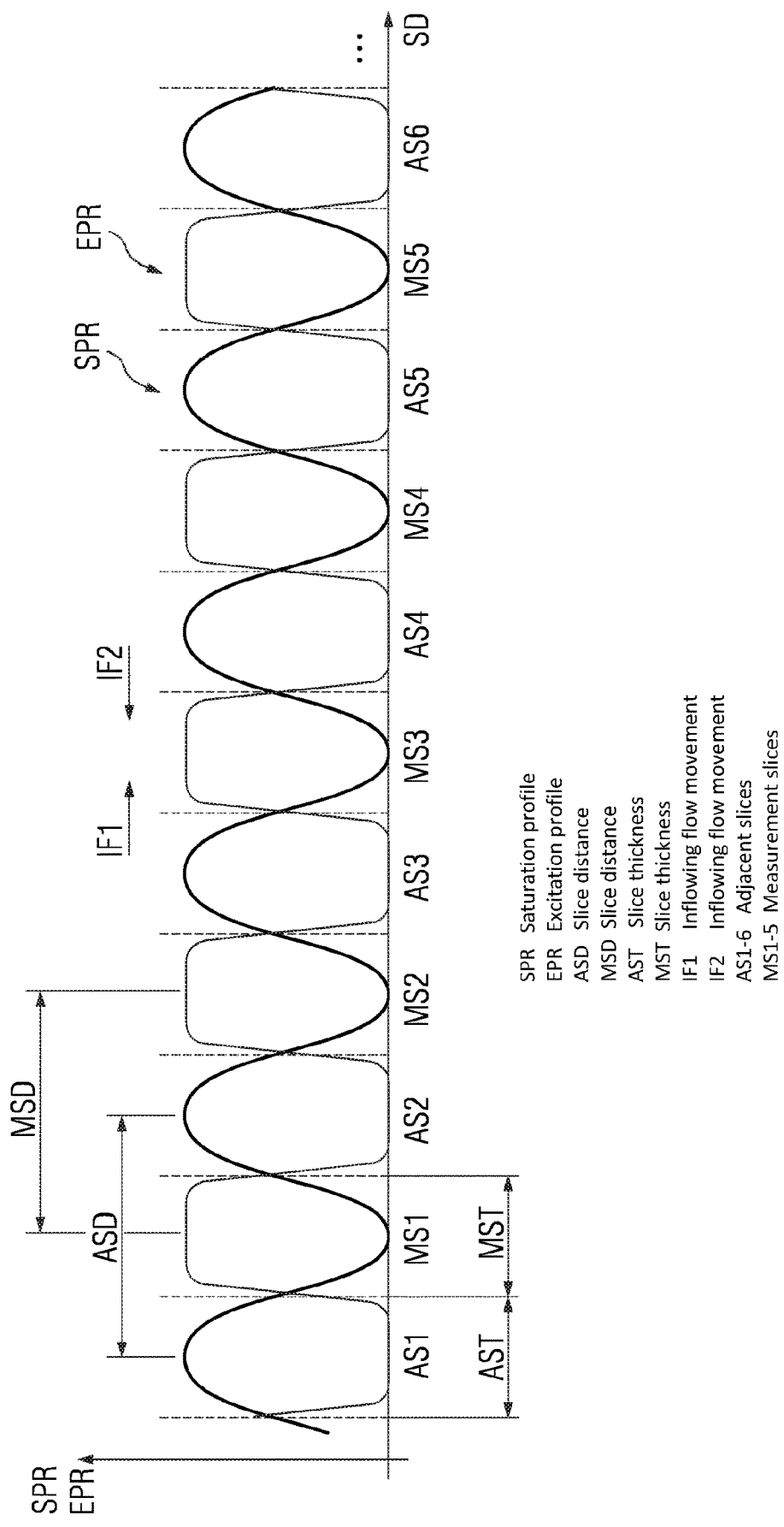
FIG. 6 depicts a diagrammatic view of an example of a saturation profile and an excitation profile.

FIG. 6 depicts a diagrammatic view of an exemplary saturation profile SPR and an excitation profile EPR. Advantageously, the saturation module SM may have a spatial saturation profile SPR which is determined as a function of at least one of the at least two measurement slices MS. Analogously, the excitation pulse EP may have a spatial excitation profile EPR which is determined as a function of at least one of the at least two measurement slices MS. In addition, the saturation profile SPR and the excitation profile EPR may be determined as a function of one another in such a way that a predefined spatial signal profile for the MR signal SIG is achieved at least for the adjacent slices AS.

In addition, five measurement slices MS1 to MS5, which are interleaved with six adjacent slices AS1 to AS6 along a common spatial dimension SD, in particular parallel to one another, are exemplarily arranged in FIG. 6. In this case, the adjacent slices AS1 and AS6 may be regarded as edge slices and the adjacent slices AS2 to AS5 as intermediate slices. The arrangement including the measurement slices MS1 to MS5 and the adjacent slices AS1 to AS6 may be referred to as a slice stack and/or slice package. The measurement slices MS1 to MS5 may each have a slice thickness MST and a slice distance MSD with respect to one another. Furthermore, the adjacent slices may have a slice thickness AST and a slice distance ASD with respect to one another.

In the exemplary embodiment shown, the measurement slices MS1 to MS6 and the adjacent slices AS1 to AS6 may each be configured to be the same with respect to slice thickness MST or AST and slice distance MSD or ASD. The illustration is merely an example, alternatively, the measurement slices MS1 to MS6 may be of identical or different design with respect to one another and/or with respect to the adjacent slices AS1 to AS5.

The spatial saturation profile SPR may specify a spatial distribution of saturated magnetization which is to be achieved by the output of the saturation module SM in act b.1). Advantageously, the spatial saturation profile SPR may be specified in such a way that the magnetization of the adjacent slices AS1 to AS6 may be selectively saturated as completely as possible by the output of the saturation module SM. The saturation profile SPR or saturation pattern thus produced may follow a periodic function which is fitted into the adjacent slices AS1 to AS6. Advantageously, the magnetization of the measurement slices MS1 to MS5 may remain virtually unaffected and/or unchanged by the output of the saturation module SM.

FIG. 6 also depicts, by way of example, for the measurement slice MS3 an inflowing flow movement IF1 and IF2, in particular a blood flow, from the immediately adjacent slices AS3 and AS4. Advantageously, the magnetization of the adjacent slices AS3 and AS4, which magnetization is transported into the measurement slice MS3 by the flow movement IF1 and IF2, may be saturated by outputting the saturation module SM in act b.1). This applies analogously to the remaining measurement slices MS1 to MS5 and adjacent slices AS1 to AS6.

Furthermore, the excitation profile EPR may specify a spatial distribution of excited magnetization which may be achieved by outputting the excitation pulse EP in act c). Advantageously, the spatial excitation profile EPR may be specified in such a way that the magnetization of the measurement slices MS1 to MS5 may be selectively excited by the output of the excitation pulse EP. Advantageously, the magnetization of the adjacent slices AS1 to AS6 may remain virtually unaffected and/or unchanged by the output of the excitation pulse EP.

The saturation profile SPR and/or the excitation profile EPR and/or the signal profile may be manually and/or semi-automatically and/or automatically specified, in particular based on the at least two measurement slices MS determined in act a).

For the spatial modulation of the excitation pulse EP and/or of the at least one saturation pulse SP, for example, a method for multi-slice excitation may be adapted, (e.g., RF pulses for energy-independent simultaneous excitation of a Power Independent Number of Slices (PINS)). These methods may be advantageously adapted and applied in relation to the saturation of the magnetization of the adjacent slices AS1 to AS6.

Figure 7:
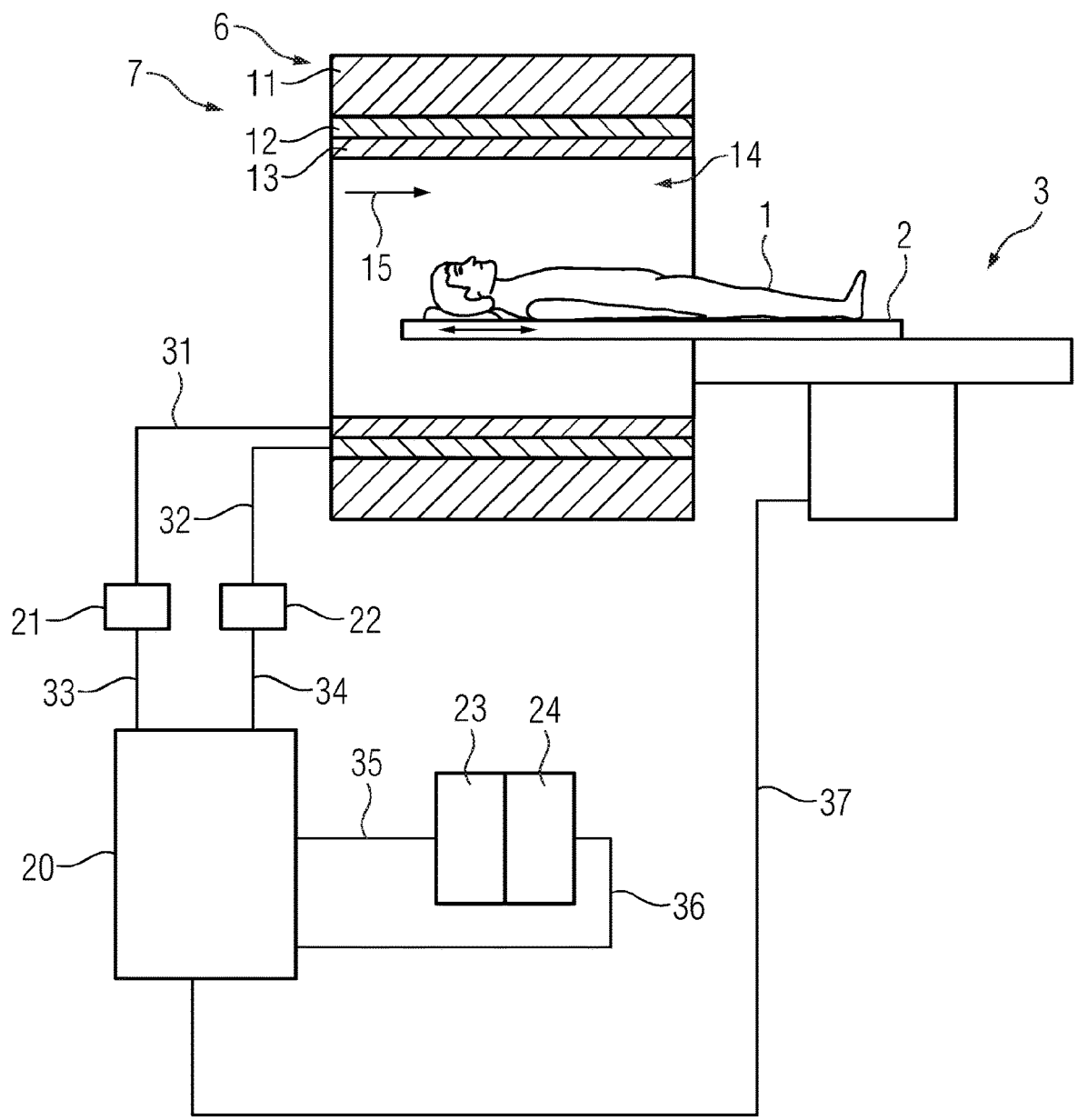
FIG. 7 depicts a diagrammatic view of an example of a magnetic resonance system.

FIG. 7 depicts a diagrammatic view of an embodiment of a proposed magnetic resonance system 7 which is configured to carry out a proposed method. In this case, the magnetic resonance system 7 includes a magnet unit 6 and an examination area 14. The magnet unit 6 furthermore includes a superconducting base magnet 11 which is configured to generate a strong main magnetic field 15 with a main magnetic field strength that is constant over time. In particular, the examination area 14 may have a cylindrical shape, wherein the examination area 14 may be enclosed by the magnet unit 6 along a lateral surface of the cylinder. In this case, the examination area 14 has at least one opening for receiving an examination object 1 and a storage facility 2. The storage facility 2 is movably mounted such that a positioning of the examination object 1 from a position outside the magnetic resonance system 7 into the examination area 14 may take place. Here, the storage facility 2 may be supported by a positioning table 3 and may be moved, in particular by a motor and/or automatically. For this purpose, a processing unit 20 may send a signal 37 to the positioning table 3. Conversely, the current positioning of the storage facility 2, in particular of the examination object 1, may be queried via the query of the signal 37 by the processing unit 20 from the positioning table 3.

Furthermore, the magnet unit 6 includes a gradient coil unit 12, which is configured to generate magnetic field gradients, in particular read gradients and/or phase encoding gradients and/or slice encoding gradients, for spatial encoding during image recording. The gradient coil unit 12 may be controlled by a gradient control unit 22. For this purpose, the gradient control unit 22 may feed a variable current 32 into the gradient coil unit 12.

The magnet unit 6 also has an RF antenna unit 13, which in the proposed exemplary embodiment is configured as a body coil. In this case, the RF antenna unit 13 is closely integrated into the magnet unit 6 and surrounds the examination area 14. The RF antenna unit 13 is configured to deflect magnetization. The magnetization comes about as net magnetization, wherein in a state of equilibrium there is a parallel alignment of nuclear spins in the main magnetic field 15. In particular, a polarization of the nuclear spins may be excited by outputting RF pulses, in particular excitation pulses EP and/or saturation pulses SP. Furthermore, the RF antenna unit 13 may be controlled by a signal 31 from an RF processing unit 21. The RF antenna unit 13 is further configured to receive MR signals SIG. Here, the RF antenna unit 13 may send a corresponding signal 31 to the RF processing unit 21. The gradient control unit 22, the RF processing unit 21, and the base magnet 6 may be controlled via the processing unit 20 of the magnetic resonance system 7. For this purpose, the signals 33 and 34 may be used bidirectionally. Alternatively or in addition, the at least one MR signal SIG may be received by an MR local coil (not shown here), which is arranged on the examination object 1 within the examination area 14. For this purpose, the MR local coil may send a corresponding signal to the RF processing unit 21.

The processing unit 20 may advantageously include a sequence control unit which is configured to convert an MR sequence, (e.g., for the saturation-prepared recording of MR image data IM), into signals for the respective components of the magnetic resonance system 7. This makes it possible to carry out an MR sequence during an MR examination of the examination object 1. Furthermore, the processing unit 20 may be configured to process the MR signals SIG received by the RF antenna unit 13 and to reconstruct the MR image data IM therefrom.

The magnetic resonance system 7 may execute an MR sequence for the saturation-prepared recording of the MR image data IM by the sequence control unit. Furthermore, the MR sequence may include an output of RF pulses, (e.g., excitation pulses EP and/or saturation pulses SP), wherein the RF pulses may be output by the RF antenna unit 13. In addition, the MR sequence may include an output of magnetic field gradients, (e.g., read gradients and/or phase encoding gradients and/or slice encoding gradients and/or spoiler gradients SG, SG' and/or SG"), wherein the magnetic field gradients may be output by the gradient coil unit 12. In this case, the MR sequence may specify a scan of the k-space for recording the at least one MR signal SIG. The RF antenna unit 13 may furthermore be configured to detect the at least one MR signal SIG and to provide it to the RF processing unit 21 or the processing unit 20. The processing unit 20 may be configured to reconstruct RECO-IM and/or provide PROV-IM the MR image data IM from the at least two measurement slices MS based on the at least one MR signal SIG.

Furthermore, the proposed magnetic resonance system 7 includes a display unit 23 configured to display parameter values of the MR sequence and/or the MR image data. For this purpose, the processing unit 20 may send a signal 35 to the display unit 23. The display unit 23 may be configured as a monitor and/or a display. Furthermore, the magnetic resonance system 7 may include an input unit 24, (e.g., a keyboard and/or a touch screen and/or a button arrangement), which is configured to send an input of a user to the processing unit 20 by a signal 36. The input unit 24 may be at least partially integrated into the display unit 23, for example, as a capacitive and/or resistive input display. Parameters and/or parameter values of the MR sequence, (e.g., a flip angle and/or a pulse duration), may be input and/or adapted by a user by the input unit 24. Furthermore, the examination volume MV and/or the at least two measurement slices MS and/or the adjacent slices AS and/or the saturation profile SPR and/or the excitation profile EPR and/or the signal profile may be specified by a user input at the input unit 24.

A control of the storage facility 2 may also be made possible via an input of a user at the input unit 24. In this case, the processing unit 20 may send a signal 37 to the positioning table 3, as a result of which an automatic and/or semi-automatic positioning of the examination object 1 relative to an isocenter of the magnetic resonance system 7 is made possible.

The diagrammatic views contained in the figures described do not depict any scale or size ratio.

Finally, it is pointed out once again that the methods described in detail above and the apparatus illustrated are merely exemplary embodiments which may be modified in a wide variety of ways by a person skilled in the art without departing from the scope of the disclosure. Furthermore, the use of the indefinite article "a" or "an" does not exclude the features concerned from also being present multiple times. Likewise, the terms "unit" and "element" do not exclude the components concerned including a plurality of interacting subcomponents, which may also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for a saturation-prepared recording of magnetic resonance (MR) image data, the method comprising:
   establishing at least two measurement slices in an examination volume of an examination object, wherein the examination volume has adjacent slices which each adjoin at least one measurement slice of the at least two measurement slices;
   outputting a saturation module comprising at least one saturation pulse for saturating a magnetization of the adjacent slices;
   outputting an excitation pulse for excitation of magnetization of at least one measurement slice of the at least two measurement slices;
   reading out an MR signal of the examination volume, wherein the outputting of the saturation module, the outputting of the excitation pulse, and the reading out of the MR signal are carried out until the magnetization of all measurement slices of the at least two measurement slices has been excited;

reconstructing the MR image data from the at least two measurement slices based on the MR signal; and providing the MR image data, wherein the establishing of the at least two measurement slices, the outputting of the saturation module, the outputting of the excitation pulse, the reading out of the MR signal, the reconstructing of the MR image data, and the providing of the MR image data are iteratively carried out, and wherein previous adjacent slices from the establishing of the at least two measurement slices are at least partially defined as measurement slices.

2. The method of claim 1, wherein the saturation module is configured to saturate magnetization of a blood flow within the adjacent slices.

3. The method of claim 2, wherein the saturation module has a spatial saturation profile which is determined as a function of the at least two measurement slices.

4. The method of claim 3, wherein the excitation pulse has a spatial excitation profile which is determined as a function of at least one measurement slice of the at least two measurement slices.

5. The method of claim 4, wherein the determination of the spatial saturation profile and the spatial excitation profile takes place in dependence on one another in such a way that a predetermined spatial signal profile for the MR signal is achieved at least for the adjacent slices.

6. The method of claim 1, wherein the saturation module has an effective flip angle of less than 90°.

7. A method for a saturation-prepared recording of magnetic resonance (MR) image data, the method comprising:

establishing at least two measurement slices in an examination volume of an examination object, wherein the examination volume has adjacent slices which each adjoin at least one measurement slice of the at least two measurement slices;

outputting a saturation module comprising at least one saturation pulse for saturating a magnetization of the adjacent slices;

outputting an excitation pulse for excitation of magnetization of at least one measurement slice of the at least two measurement slices;

reading out an MR signal of the examination volume, wherein the outputting of the saturation module, the outputting of the excitation pulse, and the reading out of the MR signal are carried out until the magnetization of all measurement slices of the at least two measurement slices has been excited;

reconstructing the MR image data from the at least two measurement slices based on the MR signal; and providing the MR image data, wherein the saturation module has a spatial saturation profile which is determined as a function of the at least two measurement slices.

8. The method of claim 7, wherein the excitation pulse has a spatial excitation profile which is determined as a function of at least one measurement slice of the at least two measurement slices.

9. The method of claim 8, wherein the determination of the spatial saturation profile and the spatial excitation profile takes place in dependence on one another in such a way that a predetermined spatial signal profile for the MR signal is achieved at least for the adjacent slices.

10. The method of claim 1, wherein the saturation module also comprises at least one tagging gradient.

11. A method for a saturation-prepared recording of magnetic resonance (MR) image data, the method comprising:

establishing at least two measurement slices in an examination volume of an examination object, wherein the examination volume has adjacent slices which each adjoin at least one measurement slice of the at least two measurement slices;

outputting a saturation module comprising at least one saturation pulse for saturating a magnetization of the adjacent slices;

outputting an excitation pulse for excitation of magnetization of at least one measurement slice of the at least two measurement slices;

reading out an MR signal of the examination volume, wherein the outputting of the saturation module, the outputting of the excitation pulse, and the reading out of the MR signal are carried out until the magnetization of all measurement slices of the at least two measurement slices has been excited;

reconstructing the MR image data from the at least two measurement slices based on the MR signal; and providing the MR image data, wherein the saturation module and/or the excitation pulse are determined as a function of a tissue parameter of the examination object, a blood flow parameter of the examination object, a relaxation parameter of the examination object, or a combination thereof.

12. A method for a saturation-prepared recording of magnetic resonance (MR) image data, the method comprising:

establishing at least two measurement slices in an examination volume of an examination object, wherein the examination volume has adjacent slices which each adjoin at least one measurement slice of the at least two measurement slices;

outputting a saturation module comprising at least one saturation pulse for saturating a magnetization of the adjacent slices;

outputting an excitation pulse for excitation of magnetization of at least one measurement slice of the at least two measurement slices;

reading out an MR signal of the examination volume, wherein the outputting of the saturation module, the outputting of the excitation pulse, and the reading out of the MR signal are carried out until the magnetization of all measurement slices of the at least two measurement slices has been excited;

reconstructing the MR image data from the at least two measurement slices based on the MR signal;

providing the MR image data; and outputting at least one spoiler gradient.

13. The method of claim 12, wherein the outputting of the saturation module and the outputting of the at least one spoiler gradient are iteratively carried out.

14. A magnetic resonance system comprising:

a processing unit configured to:

establish at least two measurement slices in an examination volume of an examination object, wherein the examination volume has adjacent slices which each adjoin at least one measurement slice of the at least two measurement slices;

output a saturation module comprising: (1) at least one saturation pulse for saturating a magnetization of the adjacent slices and (2) at least one tagging gradient;

output an excitation pulse for excitation of magnetization of at least one measurement slice of the at least two measurement slices;

readout a magnetic resonance (MR) signal of the examination volume, wherein the output of the saturation module, the output of the excitation pulse, and the readout are carried out until the magnetization of all measurement slices of the at least two measurement slices has been excited;

reconstruct MR image data from the at least two measurement slices based on the MR signal; and provide the MR image data.

15. A non-transitory computer program product comprising a computer program, wherein the computer program is configured to be loaded directly into a memory of a programmable computing unit of a processing unit, wherein the computer program, when executed in the computing unit of the processing unit, causes the processing unit to:

establish at least two measurement slices in an examination volume of an examination object, wherein the examination volume has adjacent slices which each adjoin at least one measurement slice of the at least two measurement slices;

output a saturation module comprising at least one saturation pulse for saturating a magnetization of the adjacent slices, wherein the saturation module has an effective flip angle of less than 90';

output an excitation pulse for excitation of magnetization of at least one measurement slice of the at least two measurement slices;

readout a magnetic resonance (MR) signal of the examination volume, wherein the output of the saturation module, the output of the excitation pulse, and the readout are carried out until the magnetization of all measurement slices of the at least two measurement slices has been excited;

reconstruct MR image data from the at least two measurement slices based on the MR signal; and provide the MR image data.

* * * * *